(12) United States Patent
Mars et al.

(10) Patent No.: US 12,052,816 B1
(45) Date of Patent: Jul. 30, 2024

(54) SMART RING AND METHODS FOR MANUFACTURING

(71) Applicant: Ouraring Inc., San Francisco, CA (US)

(72) Inventors: Denis Mars, San Francisco, CA (US); Simon Ratner, San Francisco, CA (US); Curt C. von Badinski, San Francisco, CA (US)

(73) Assignee: Ouraring Inc., San Francisco, CA (US)

( * ) Notice: Subject to any disclaimer, the term of this patent is extended or adjusted under 35 U.S.C. 154(b) by 9 days.

(21) Appl. No.: 17/326,201

(22) Filed: May 20, 2021

Related U.S. Application Data (60) Provisional application No. 63/029,004, filed on May 22, 2020, provisional application No. 63/027,774, filed on May 20, 2020, provisional application No. 63/027,769, filed on May 20, 2020.

(51) Int. Cl.
| | |
|---|---|
| *H05K 1/18* | (2006.01) |
| *G06F 1/16* | (2006.01) |
| *H05K 1/02* | (2006.01) |
| *H05K 3/28* | (2006.01) |
| *H05K 3/36* | (2006.01) |

(52) U.S. Cl.
CPC ........... *H05K 1/0271* (2013.01); *G06F 1/163* (2013.01); *H05K 3/284* (2013.01); *H05K 3/36* (2013.01); *H05K 2201/09018* (2013.01); *H05K 2201/10098* (2013.01); *H05K 2201/10106* (2013.01); *H05K 2201/10151* (2013.01)

(58) Field of Classification Search
CPC ........ H05K 1/0271; H05K 3/284; H05K 3/36; H05K 2201/09018; H05K 2201/10098; H05K 2201/10106; H05K 2201/10151; G06F 1/163

USPC .................................................... 361/679.03
See application file for complete search history.

(56) References Cited

U.S. PATENT DOCUMENTS

| | | | | |
|---|---|---|---|---|
| 9,943,724 | B2* | 4/2018 | Mestas | G16H 20/30 |
| 2014/0372940 | A1* | 12/2014 | Cauwels | A61B 5/024 |
| | | | | 715/799 |
| 2015/0120020 | A1* | 4/2015 | Armstrong | G04G 21/025 |
| | | | | 700/91 |
| 2016/0342176 | A1* | 11/2016 | Han | G04G 17/06 |
| 2017/0018248 | A1* | 1/2017 | Na | G06F 3/0346 |
| 2019/0067968 | A1* | 2/2019 | Guo | G06F 1/163 |
| 2019/0298188 | A1* | 10/2019 | Dana | A61B 5/02116 |

* cited by examiner

*Primary Examiner* — Binh B Tran
(74) *Attorney, Agent, or Firm* — Holland & Hart LLP (57) ABSTRACT

A method for fabricating a smart ring includes receiving a printed circuit board having a processor, a memory, a temperature sensor, a wireless transceiver and a perturbation sensor, receiving a power source with a first radius of curvature within a range of 7 mm to 15 mm, coupling the printed circuit board and the power source together to form a first assembly with the first radius of curvature, encapsulating the first assembly to form a second assembly with a second radius of curvature wherein the first radius is larger than the second radius, and wherein the second assembly includes a plurality of physical anchors, determining a first ring size from a plurality of ring sizes, and coupling a band to the second assembly via the plurality of physical anchors to form an enclosed circle-like shape in response to the first ring size, wherein the band is characterized by the second radius.

20 Claims, 5 Drawing Sheets

SMART RING AND METHODS FOR MANUFACTURING

CROSS-REFERENCE TO RELATED APPLICATIONS

The present invention claims priority to and is a non-provisional of U.S. Pat. App. No. 63/027,769 filed May 20, 1920, a non-provisional of U.S. Pat. App. No. 63/029,004 filed May 22, 1920, and a non-provisional of U.S. Pat. App. No. 63/027,774 filed May 20, 1920. These applications are incorporated by reference herein, for all purposes.

BACKGROUND

Embodiments of the present invention relate to smart rings and manufacture thereof.

The inventor of the present invention has been a pioneer in the development, manufacture and selling of smart rings in the industry. Because these devices have such small form-factors, it has required great innovation and novel manufacturing techniques to successfully mass produce smart rings. Such intricate devices have typically been very expensive to manufacture and, accordingly, have been very expensive for consumers.

One specific factor that greatly increases cost is the need to produce smart rings of different sizes. Typical ring sizes range from size 5 (approximately 16 mm in diameter) to size 13 (approximately 22 mm in diameter), and with half sizes, it typically requires a smart ring manufacturer to manufacture and stock of over seventeen different devices. Accordingly, a smart ring manufacturer will disadvantageously have substantial costs for making different sizes of rings and substantial capital tied up in inventory.

In light of the above what is desired are smart rings and methods for manufacture thereof without the drawbacks described above.

SUMMARY

In some embodiments, the smart ring may include an electronics subassembly portion and a band portion, the combination which forms the O-shaped ring. In some cases, the electronics subassembly portion spans a sector of the ring and is formed of a shell of plastic, metal, ceramics, silicone material, wood, or other material. This shell may encapsulate the electronics of the smart ring including a main control unit, wireless communications, a power source, an output indicator (e.g. display, LED light, haptic generator, speaker, or the like), a biological sensor (e.g. thermometer, heart rate sensor, blood oxygen sensor, or the like), a perturbation sensor (e.g. accelerometer, gyroscope, pressure sensor, magnetic sensor, or the like), and the like. In various embodiments, one or more of these components may be mounted upon a flexible or rigid printed circuit board. The band portion may span the remaining sectors of the ring to form the O-shape and may be formed from a material such as silicone, wood, metal, ceramics, or the like. The band portion may be pre-formed and coupled to the electronics subassembly portion, and in some cases may be injection molded adjacent to the electronics subassembly portion, or the like.

Examples of smart wearable devices includes smart rings having sensors for periodically determining biological data of users, as mentioned above. Other examples may also include additional sensors for periodically determining physical perturbations of the smart ring, also mentioned above. In some embodiments, the periodic biological data and/or periodic physical perturbations can be used to determine anomalous health conditions of the user. For example, a temperature increase not accompanied by any movement determined by an accelerometer may indicate the user may potentially have a health issue; whereas a temperature increase that is accompanied by vigorous movement determined by an accelerometer may not indicate the user may have a health issue, but suggest the user is exercising.

In additional embodiments, machine learning algorithms may be used to derive baseline biological data models for the user based upon the user's biological data when they are healthy. As an example, assuming the user is healthy when they first receive a smart ring, the biological data (and sometimes perturbation data) is gathered over a particular time period, for example one week, two weeks, or the like. Such data may be uploaded to a paired smart device running embodiments of software applications, described below. In some embodiments, the software application utilizes machine learning algorithms to process the data and to determine a baseline biological data model for the user. Subsequently, new incoming biological data of the user can also be uploaded to the smart device, and this data is compared to the user's baseline biological data model to determine deviations thereof. If the number of deviations, magnitudes of deviations, or the like, exceed a defined threshold, the smart phone may signal a potential anomalous health condition for the user.

In some embodiments, if anomalous health condition is detected, the user may be notified (e.g. alert, banner, image, sound, vibration, text message or the like) by the smart phone. In some embodiments, a notice may be provided to the smart ring, such that the smart ring flashes yellow, outputs a sound, vibrates, or the like. In some embodiments, if there is an anomaly, the smart phone or smart ring may provide a notice to a third party device or server. For example, an identity authentication server, that is coupled to an identity reader device (coupled to controlled access point), may be notified. Then when the user presents their identity credentials (e.g. via mobile access (BLE) identity credentials) and attempts to enter the controlled access point (e.g. security gate, security door, elevator, or the like), although they are authorized (e.g. a qualified employee, a vetted agent, or the like), the user may still be denied access, because of the potential anomalous health condition.

According to one aspect, a method for fabricating a smart ring is disclosed. A process may include receiving a printed circuit board having a plurality of components including a processor, a memory, a temperature sensor, a wireless transceiver and a perturbation sensor, receiving a power source characterized by a first radius of curvature within a range of about 7 mm to 11 mm, and coupling the printed circuit board and the power source together to form a first assembly characterized by the first radius of curvature. A method may include encapsulating at least a first portion of the first assembly to form a second assembly, wherein the second assembly is characterized by a second radius of curvature and a third radius of curvature, wherein the third radius is larger than the first radius, and the first radius is larger than the second radius, and wherein the second assembly includes a plurality of physical anchors, determining a first ring size from a plurality of ring sizes, and coupling a band to the second assembly via the plurality of physical anchors to form an enclosed circle-like shape in response to the first ring size, wherein the band is characterized by the second radius.

According to another aspect, a smart ring is disclosed. An apparatus may include a first assembly characterized by a first radius of curvature having therein a second assembly characterized by a second radius of curvature within a range of 7 mm to 11 mm, or the like wherein the second radius is larger than the first radius, including a printed circuit board having a plurality of components including a processor, a memory, a temperature sensor, a wireless transceiver and a perturbation sensor, a power source characterized by the first radius of curvature, a plurality of interconnects coupled between the printed circuit board and the power source, an encapsulating material disposed about at least a first portion of the second assembly, and a plurality of physical anchors. A device may include a band coupled to the first assembly via the plurality of physical anchors forming an enclosed circle-like shape characterized by the first radius.

DRAWINGS

In order to more fully understand the present invention, reference is made to the accompanying drawings. Understanding that these drawings are not to be considered limitations in the scope of the invention, the presently described embodiments and the presently understood best mode of the invention are described with additional detail through use of the accompanying drawings.

DETAILED DESCRIPTION

In various embodiments, a smart wearable device may be embodied as a smart ring, smart tag, smart glasses, smart headphones, and the like. In examples described herein below, a novel smart ring is disclosed. In various embodiments, a smart ring may include a power supply such as a lithium ion battery, lithium polymer battery, an ultracapacitor, carbon nanotube capacitor, button batteries or the like. In various embodiments, the power supply is curved in shape, as illustrated below. In the case of discrete batteries, e.g. button batteries, these batteries should also be coupled in a curved orientation, to match the curvature of the ring form factor.

In various embodiments, power management and charging circuitry is typically provided to control charging of the power supply. In some examples, charging may be facilitated by and external power source, such as an electrical source, magnetic source, radio frequency (rf) source, light or laser source, heat source, or the like. In various cases, the charging circuitry may include components appropriate for the charging source, such as electrical contacts, metal coils, solar or light power conversion regions, thermoelectric generation components, or the like.

Additionally, in some embodiments of a wearable device, self-power-generation components may be included that generate power in response to movement of the wearable device, e.g. smart ring, bio patch, wrist device, etc. Some examples may include a movable magnet or magnetic liquid moving that passes back and forth through a coil as the person walks to generate electricity. Other examples may include a charged liquid passed back and forth through a ferromagnetic material that generates the electricity. In some cases, a channel or tube for the liquid may span only a sector of the ring, and in other cases, the channel or tube may run fully around the ring. In some embodiments, the tube may be tapered in the vicinity of the energy producing coil or ferromagnetic material. Accordingly, as the user moves, the liquid may move in the tube at a first velocity, and as the liquid reaches the tapered section, the liquid velocity may increase to a higher, second velocity. In this example, the higher velocity liquid may induce greater electricity generation. In various embodiments, usable ranges of viscosity of the liquid may be determined based upon power requirements and predicted user motion.

In the embodiments below, other functional elements may include a microcontroller unit having a wireless transmitter. In various embodiments, the microcontroller unit may perform identification functionality, e.g. providing a non-permanent, ephemeral ID's output, communicating with authentication services, interfacing with other smart devices, interfacing with identity reader devices, facilitating other types of authentications, such as FIDO 2, or the like. Examples of wireless transmissions that may be supported includes Bluetooth, ultrawide band (UWB), Zigbee, rf, WIFI, cellular, 4G, 5G, and the like.

In some embodiments, memory elements may be provided for storage of data, computer code executable upon the microcontroller; a secure element for storage of secure data, such as encryption keys, tokens associated with financial accounts (e.g. credit cards, debit cards, device account number (DAN) etc.), tokens provided by embodiments of the present invention, described above, and the like. In some cases, NFC communication is provided enabling financial transactions using data stored within the secure element and point of sale (POS) terminals, and the like.

In various embodiments, a number of sensors may be provided to sense a variety of parameters associated with the user. In some embodiments, a temperature sensor is provided to sense the temperature of the user adjacent to the wearable device. In some examples, a temperature sensor may utilize: a thermocouple, a thermistor, a resistor temperature detector, a semiconductor sensor, an infrared sensor, or the like. Depending upon the embodiment, one or more temperature conductive contacts, e.g. metal, may be used; an infrared transparent (or substantially transparent) covering may be disposed above an infrared sensor; and the like.

In other embodiments, a heartbeat, a blood oxygen sensor, or the like may be provided, typically based upon reflection or transmission of LED light relative to the user (e.g. finger, earlobe, ear canal, temple, etc.), to monitor the heartbeat, heartbeat pattern, or the like of the user. Other types of biometric sensors may also be provided, such as a blood-vessel sensor, a fingerprint sensor, and the like. In one embodiment, a specific region of the smart ring may be electrically insulated from other portions of the smart ring that contact the user's fingers. In such embodiments a user may place a finger from their other hand upon the specific region to enable the ring to sense a user's EKG, ECG, or the like. In various embodiments, these types of biometric sensors may be used for authenticating the user on the device. For example, using a sensor on the interior of the ring, the smart device (e.g. smart ring, smart earbud, smart glasses) may be locked every time the device is taken off, and not unlocked until the proper biometric credentials are presented. In other embodiments, various biometric data may be used for health monitoring purposes, as disclosed herein.

In some embodiments, additional sensors may include accelerometers, gyroscopes, magnetometers, pressure sensors, or the like, that capture movements of the smart device. In various embodiments, the captured perturbation data may be used for a number of functions. One function is the capturing of user movements and recognition of these movements as one or more pre-defined gestures. Upon determination of the gestures, the smart ring may perform specific functions, direct an external device to perform a function, or the like. In other embodiments, the captured perturbation data may be used to determine biometric characteristics of the user, e.g. gait, stride length, and the like.

In some embodiments, sensors described above, as well as additional sensors may be used for the user to select different modes of operation and to interact with the smart devices. As merely an example, a pressure sensor may detect a user pressing upon the smart device; a capacitive sensor may detect whether the user is wearing the smart device; a microphone may detect spoken user commands; one or more physical buttons may detect a user depressing a button; and the like. In other examples, a magnetic sensor may determine orientation of the ring with respect to a global magnetic field, the presence and orientation of a local magnetic field (device) with respect to the ring, or the like. In some embodiments, any number of outputs may be provided to give the user feedback. Examples of user outputs includes a micro display (e.g. OLED), one or more status LEDs, vibrational (haptic) feedback, audio outputs, SMS output and the like. In some embodiments, a smart ring is disclosed, as illustrated below.

Figure 1A:
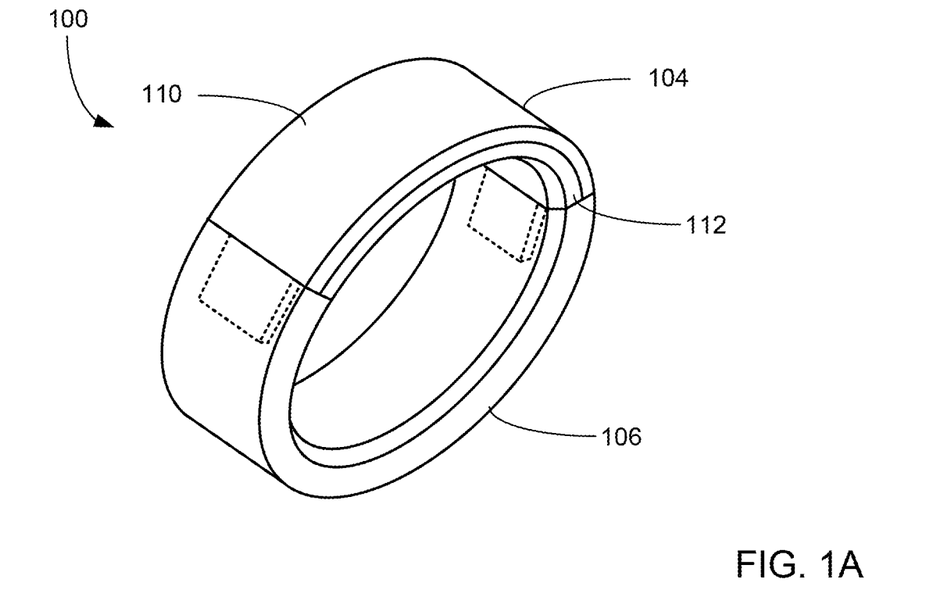
FIGS. 1A-1C illustrate some embodiments of the present invention.
Figure 1B:
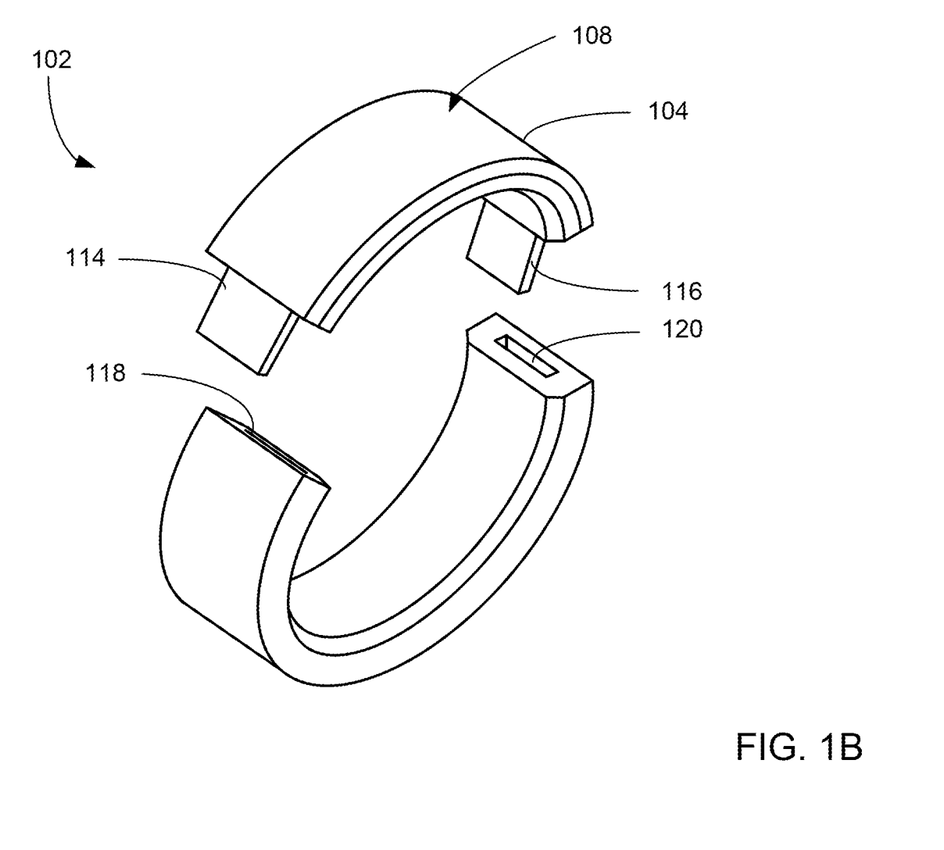
Figure 1C:
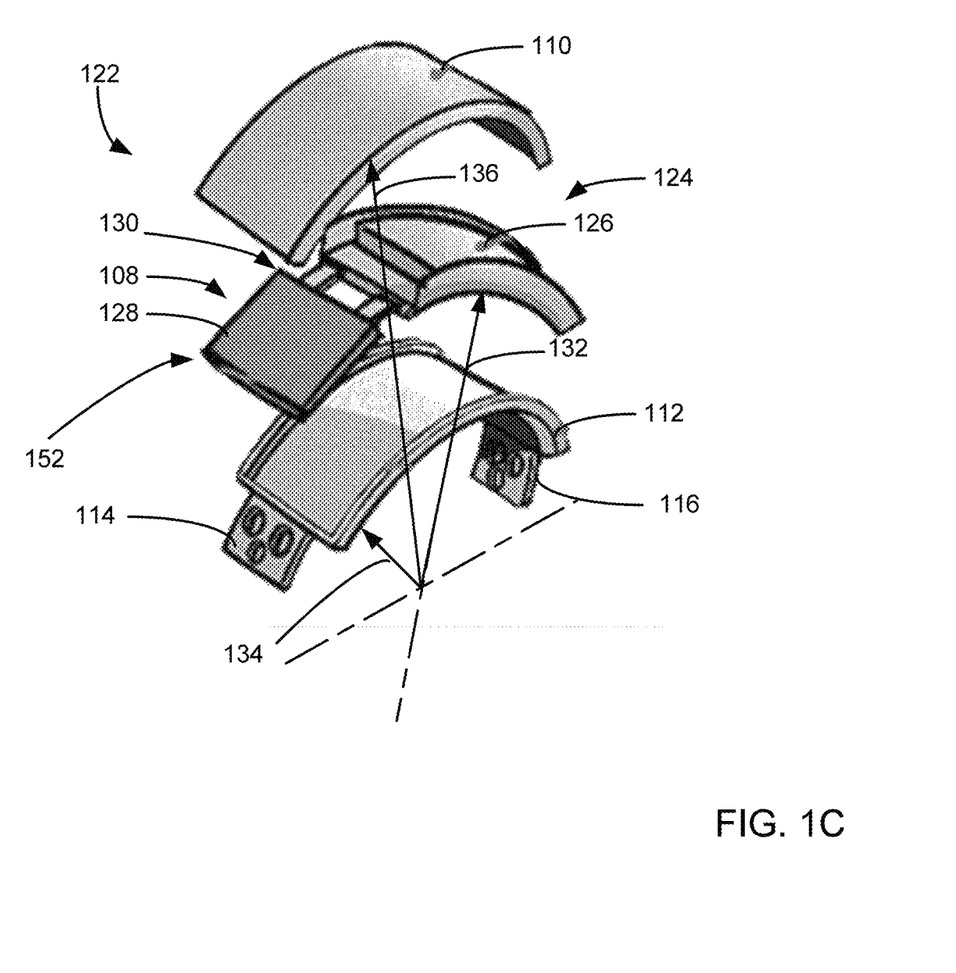

FIGS. 1A-C illustrate some embodiments of the present invention. More specifically FIG. 1A illustrates an assembled embodiment 100, FIG. 1B illustrates an exploded embodiment 102 of a smart ring (a smart device), and FIG. 1C illustrates an exploded embodiment 122 of enclosure portion 104 of the smart ring. In some embodiments, the smart ring may include two major components, an enclosure portion 104 and a band portion 106. The enclosure portion 104 may include many of the electronics components 108 described above, or fewer, depending upon desired capability. As illustrated in FIG. 1C, the enclosure portion 104 may include a curved enclosure made of: plastic, epoxy, ceramics, silicone, metal, wood, and the like. In various embodiments, an enclosure 104 may include two or more shells, e.g. upper enclosure 110 and lower enclosure 112 that include an interior region 124 into which the electronics components 108 mentioned above may be disposed. As an example, upper enclosure 110 and lower enclosure 112 may be made of metal, ceramics, plastics, combinations thereof, or the like, and may be welded, glued, screwed together, or the like. In another example, the electronics components 108, described above, e.g. a curved battery 126, printed circuit board (PCBA) 128, and interconnects 130 may be produced (a first assembly 152) and placed within a mold. Next, a plastic material, silicone material, epoxy material, or the like may be injected into the mold to form an over molded material 104 (a second assembly). As can be seen in FIG. 1C, curved battery 126 is characterized by a first radius of curvature 132, and enclosure portion 104 is characterized by a second radius of curvature (an interior radius) 134 and a third radius of curvature (an outer radius) 136.

As illustrated, the enclosure portion 104 may be curved and may be rigid or semi-flexible. For example, in some cases, the enclosure portion 104 is rigid and is characterized by a relatively fixed interior radius of curvature 134. In various embodiments, it is contemplated that different versions of the enclosure portion may be necessary to be used when manufacturing smart devices of different interior radius of curvatures, e.g. different ring sizes, and the like. As merely examples, a first rigid enclosure may have an interior radius of curvature 132 of about 7.6 mm to be used for ring sizes 4 through 5, a second rigid enclosure may have an interior radius of curvature of about 10 mm to be used for ring sizes 9 through 10, and the like. In contrast, a first semi-flexible enclosure may have an interior radius of curvature of about 7.8 mm to be used for ring sizes 4, 4.5, 5, 5.5 and 6, a second semi-flexible enclosure may have an interior radius of curvature of about 9 mm to be used for ring sizes 6, 6.5, 7, 7.4, 8, 8.5 and 9, and the like. In various embodiments, the enclosure portion 104 may include one or more anchoring extensions or indentations 114 and 116. These anchors 114 and 116 may provide retaining mechanisms 118 and 120 for a band portion 106. In some portions, the band portion 106 may be made of any of a variety of materials, such as plastic, silicone (e.g. liquid silicon rubber), epoxy, metal, stone, wood, or the like. In some embodiments, the enclosure portion 104 discussed above may be placed into a mold, and the band portion 106 may be injected therein to fasten to the anchor portions 114 and 116. In other embodiments, the band portion 106 may be separately constructed and fastened to the anchors 114 and 116 of the enclosure portion 104, in the factory, or by an end user. Many different shapes for anchors 114 and 116 are contemplated, such as a reverse-keystone, anchors with holes which pair with projections within retaining mechanisms 118 and 120, and the like.

In various embodiments, a smart wearable device 100 may be embodied as a smart ring, smart tag, smart glasses, smart headphones, and the like. These devices may be electrically charged through a standardized port (USB-C, USB, or the like) or custom contact region, may be wirelessly charged by rf or magnetic signals, may be wirelessly charged by solar or laser light, and the like. Additionally, in some embodiments, self-charging capability, e.g. heat differential, and the like, may also be included. Examples of external charging systems may include direct electrical power (via electrical conductors), magnetic or rf induction, charging based upon light, or the like.

In some embodiments, two smart rings may worn by a user. In these examples, gestures using both hands of a user may be used for providing instructions for the smart rings, smart devices coupled with the smart rings, or other external computing device. In some examples, when a user moves both of their hands away from or towards each other, the gesture that is interpreted is a zoom-in or zoom-out command for an external display device; when a user moves a right hand towards or away the left hand, while maintaining their left hand stationary (detected via accelerometers, etc.), the gesture that is interpreted is a next or previous command for an external computing device (e.g. next page or previous page, next track or previous page, next image or previous page, next document or previous document, pan right or pan left, etc.); and the like. In light of the present patent disclosure, one of ordinary skill in the art will recognize many other functions and gestures with two hands that are within the scope of other embodiments of the present invention.

Figure 2A:
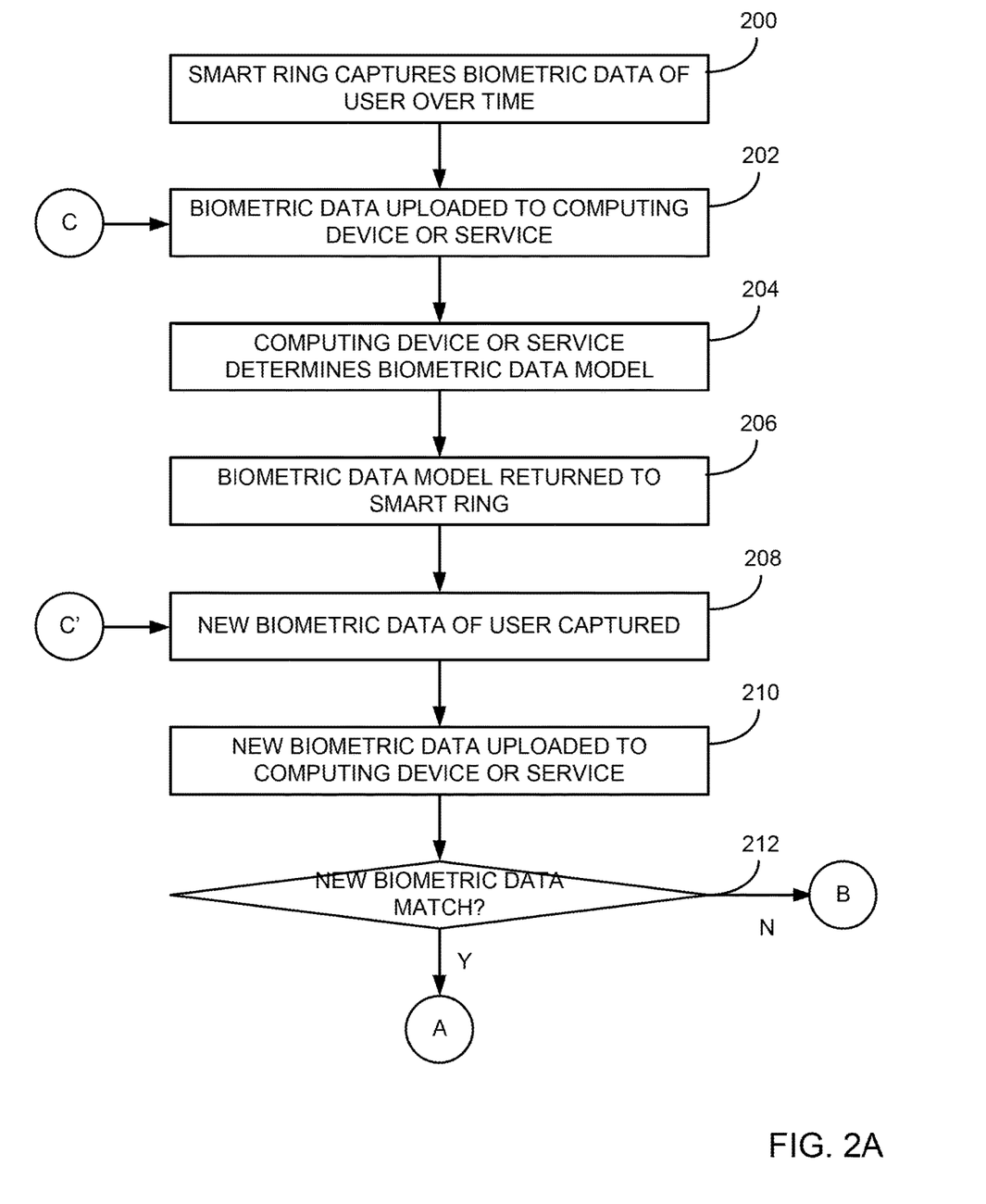
FIGS. 2A-B illustrates some embodiments of the present invention.
Figure 2B:
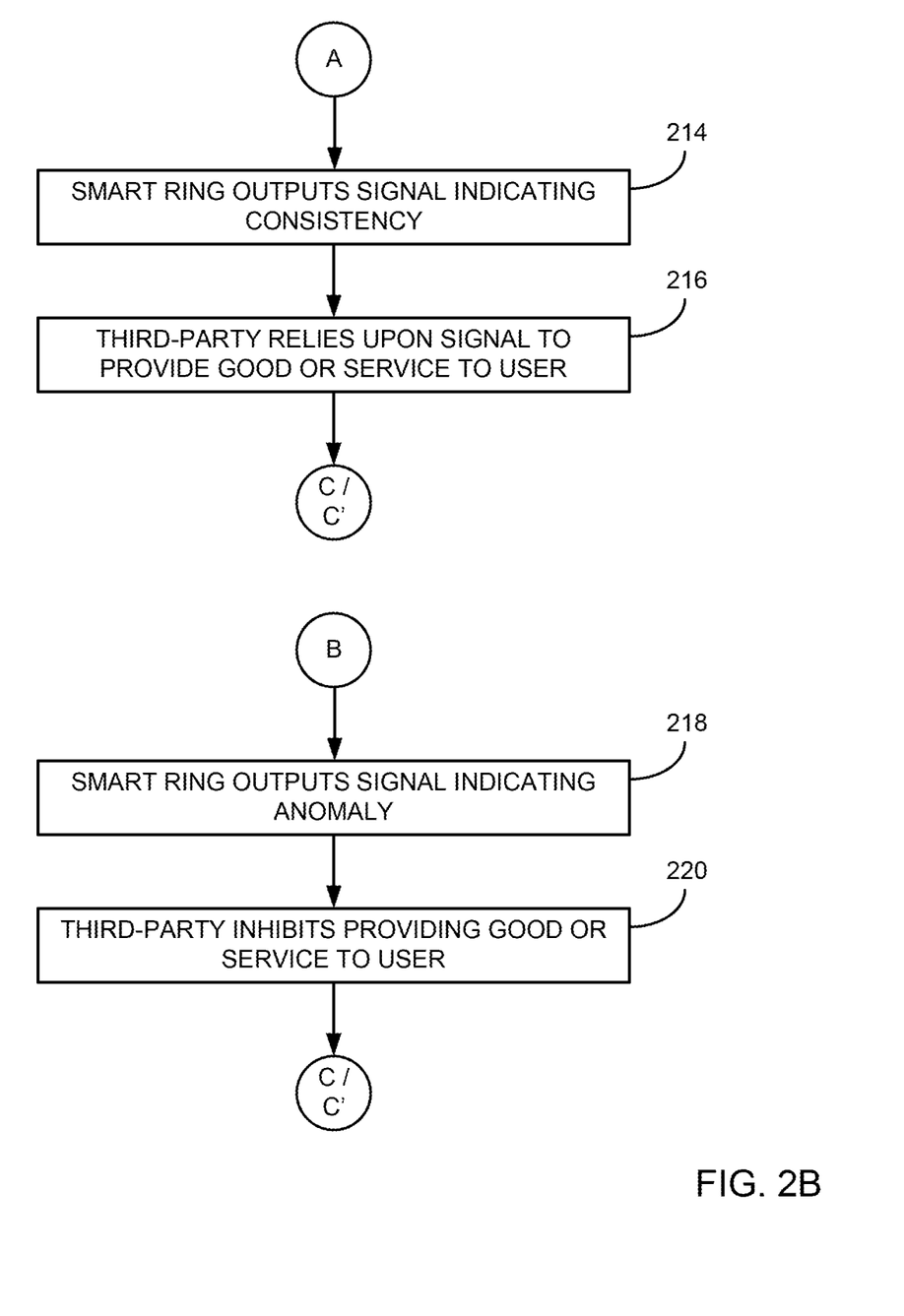

FIGS. 2A-B illustrates a block diagram of a process according to some embodiments. As illustrated and will be described below, a smart ring may capture biometric data of the user over a certain time period, step 200. The biometric data may be uploaded to a paired smart device (e.g. smart phone), a remote server, a cloud service, or the like, step 202. The biometric data may then be processed to form a biometric model for the user, step 204. The biometric model may then be returned to the paired smart device, the smart ring, or the like, step 206.

Subsequently, new biometric data is captured by the smart ring, typically over a time period, step 208. In some cases, the new biometric data may be uploaded to the paired smart device, or the like, step 210. The paired smart device, the smart ring, or the like may then determine if the new biometric data is inconsistent or consistent with the biometric model, step 212.

In various embodiments, the process described above may be repeated. More particularly, the newly acquired data may be incorporated into the biometric model and the process may return to step 202, or the newly acquired data may be ignored, and the process may return to step 208.

In some cases, if the new biometric data is consistent, the smart ring may be directed to indicate the consistency, step 214. Third parties may then provide goods or services to the user, based upon the consistency, step 216. As examples, the smart ring may output a green-colored light (via LED) for the user or third-parties to observe; the smart ring may output a healthy signal (via NFC, UWB, BLE, etc.), that may be electronically read by a restricted-access door, gate, check-in kiosk, or the like; and the like. In cases where the new biometric data is anomalous, the smart ring may output a red-colored light for the user or third-parties to observe, step 218. Additionally, the smart ring may pass an anomalous signal electronically (or optically) to third-party devices, which in turn may inhibit providing the user goods or services based upon the anomalous signal, step 220. In other embodiments, the third party devices may default to inhibiting providing the goods or services in absence of a consistency signal.

In some cases, whether the new biometric data is consistent or not may be combined with other functions of the smart ring. For example, in some cases, the smart ring may include functionality such as storing and providing tokens, financial data, and the like to third-party devices. In such cases, the smart ring may allow output of such data if the user is authorized (e.g. fingerprint verification, blood vessel pattern matching, proper PIN entry) and if the new biometric data is consistent with the biometric model (e.g. healthy); and the smart ring may inhibit output of such stored data if the new biometric data is not consistent with or is anomalous compared to the biometric model.

In some embodiments, the biometric data, e.g. heartbeat data, user temperature data, blood oxygen, or the like, as well as perturbation data, e.g. accelerometer data, pressure data, gyroscopic data, and the like may be uploaded to a paired smart device for further processing. In some examples, the paired smart device may be a smart phone, computer, tablet, or the like. In various embodiments the paired smart device may determine whether the user's biometric data exceeds particular criteria, e.g. elevated heart rates, elevated temperatures, reduced blood oxygen, increased blood pressure, or the like. Such abnormal biometric data readings may indicate that the user is not healthy.

In various embodiments, the perturbation data or other data is also processed by the paired smart device (or the smart ring itself) to help reduce the incidences of abnormal biometric notifications. For example, for a user, an elevated heartbeat rate or temperature may be due to the user working out, running, or the like. In such cases, an accelerometer, gyroscope, or the like will typically register strenuous and possible repetitive motions. Accordingly, a using application such as a learning algorithm, or the like running upon the paired smart device (or the smart device, remote server, cloud service, etc.), it may recognize that when it senses increased heartrates or high temperatures along with high magnitude accelerations, the user is exercising and it does not indicate that the user is unhealthy. Other cases where the user may have elevated biometric readings along with high magnitude accelerations may include the user at an amusement park, participating a motor sport, or the like. As above, such cases should not typically indicate a health anomaly. As merely another example, a reduction in user blood oxygen saturation (biometric data) might be accompanied by an elevation gain (perturbation data). In such cases, the user may be driving or hiking up a mountain, and the perturbation data (e.g. elevation) may be determined by a barometer, GPS-based map elevation, or the like. In this situation, the biometric data and the perturbation data should not normally indicate a health anomaly. In other words, the reduction in user blood oxygen saturation may be attributed to the high elevation.

In contrast to the above, if a user's temperature or heart rate increases above a certain threshold in the middle of the night, without substantial perturbation data, the smart phone may indicate a health anomaly. Also, if a user's blood oxygen saturation decreases by a certain percentage or below an absolute percentage, without substantial perturbation data, the smart phone may also indicate a health anomaly. In light of the above, other biometric/perturbation pairs may be used by the smart device to indicate whether the user may have a health anomaly or not.

In other embodiments, the biometric data, e.g. heartbeat data, user temperature data, gait data, and the like may be captured over days, weeks, or months and uploaded to a paired smart device (or the smart wearable, remote server, cloud service) for further processing. In various embodiments, the paired smart device is a smart phone. The captured data may be used by a smart phone, or by a back end cloud service to determine a baseline model for the biometric data for the user, e.g. using machine learning or artificial intelligence libraries (TensorFlow). In particular, for a first period of time while the user is healthy and going about their day normally, captured biometric data may be processed by an artificial intelligence or machine learning processes to determine a user model for the biometric data. In some examples, if the user washes their hands in cold water or hot water, the sensed user temperature should spike down or up, respectively, before returning to normal. Temperature models are expected to ignore such short-term perturbations in temperature readings. In other examples, if the user goes runs three-times a week, the sensed user heartbeats should be elevated for that period of time and for some time afterwards. Additionally, running may be determined by an accelerometer during the same time period. Heart rate baseline models are expected to also ignore or deemphasize these short-term perturbations in heartbeat data, especially if there is high accelerometer perturbations at the same time. In various embodiments, multiple models may be determined and stored in the cloud-based server or on the paired smart phone.

Subsequently, as the smart device captures new biometric data throughout the day, these new biometric data readings may be compared against one or more models (e.g. historical models) to determine if there are deviations from the models. In various embodiments, it is contemplated that the paired smart phone or the smart wearable (e.g. ring, earbuds, glasses, etc.) may perform the matching processes. In some cases, the baseline biometric models may be periodically updated, for example, on a rolling basis for the past few weeks, months, or the like.

In some embodiments, if the smart wearable device, or smart device paired to the smart wearable device determines that the newly captured user data (e.g. temperature, heartbeats, blood oxygen saturation, gait, or the like) is consistent with the user's historical model for a certain duration of time, e.g. 7 days, 14 days, or the like, the smart wearable device may provide a first indication to the user, e.g. display a green color for an LED, whereas if the newly captured data is inconsistent with the user's historical model, e.g. elevated temperature, elevated heartbeat rate, or the like, the smart wearable device may provide a second indication to the user, e.g. display a yellow color for the LED.

Additionally, in various embodiment, when coupled to an identity reader device, coupled to a controlled access point, an authentication server, the status (healthy or not-healthy) of the newly captured data may be provided. As an example, when coupled to a device (e.g. presence sensing identity reader device, authentication server, other smart device), if the new user data is inconsistent with their model, the smart device may send a yellow flag to the other device. In some examples, if an authorized employee is attempting to enter a building, but a yellow flag is provided by their smart ring, entry may be denied. For example, the identity reader device may receive the flag and although a valid identification token to enter is provided, the identity reader may not direct peripheral device (e.g. door, gate, elevator, or the like) to open. In other examples, in the case of third-party transportation, if the smart ring provides a yellow flag, a taxi or hired car may be denied, boarding of a vessel (e.g. ship, airplane, train) may be denied. In various embodiment, in order to reduce the chance of the user simply taking off or turning off their smart device, boarding, renting, or the like may require a valid electronic token, and a healthy indication, as described above.

In various embodiments, in a retail establishment, restaurant or the like, a kiosk may be provided that indicates the status of users within that facility. For example, if all of the servers have smart rings, or the like, and for every day during the previous two weeks, the user's biometric data (e.g. temperature) is consistent with their historical model, the kiosk may show names of the servers and green lights next to their name. In this way, a user entering the facility may have a certain level of confidence that the establishment is safe. Additionally, for every user in the facility having a smart ring and who is consistent with their historical models, additional green lights may be displayed on the kiosk. Accordingly, if a crowded bar has 100 green lights, a user may feel safer visiting that establishment.

In various embodiments, if the user's current readings do not match the user's historical model (e.g. a baseline model), the smart device may also contact a third party, e.g. a community health server, a company HR administrator, or the like. In various embodiments, the readings of the user may be based upon temperature, heart rate, blood oxygen saturation, blood pressure, or the like. Additionally, the historical model may be based upon any of such user readings (e.g. temperature, heart rate, etc.) when the user is healthy. This healthy state data may be processed by machine learning algorithms on a smart phone, in the cloud, or the like to determine a baseline model for the reading (e.g. a baseline temperature model, a baseline blood oxygen saturation model, etc.) Typically, these models may first be based upon a generic model (i.e. machine learning from data from hundreds or thousands of users) and may then be customized for each user, based upon machine learning algorithms using the specific readings, characteristics, physiology for the user. Over time, a user's baseline models may vary based upon additional machine learning algorithms, for example because the user loses weight, the user exercises more, the user develops a health condition, and the like.

In response, a smart device paired to the smart ring or a third party server may contact the user, via e-mail, text, SMS, phone call, vibration, or the like to communicate the anomalies or deviations from a baseline model. In some embodiments, the indication may be used to restrict a user from entering certain locations or using certain services. For example, if the smart ring is coupled to an identity reader infrastructure provided by the assignee of the current provisional application, authorization by an authentication server may be denied, a computer login may be denied, and the like, when there is a user health deviation or anomaly.

Figure 3:
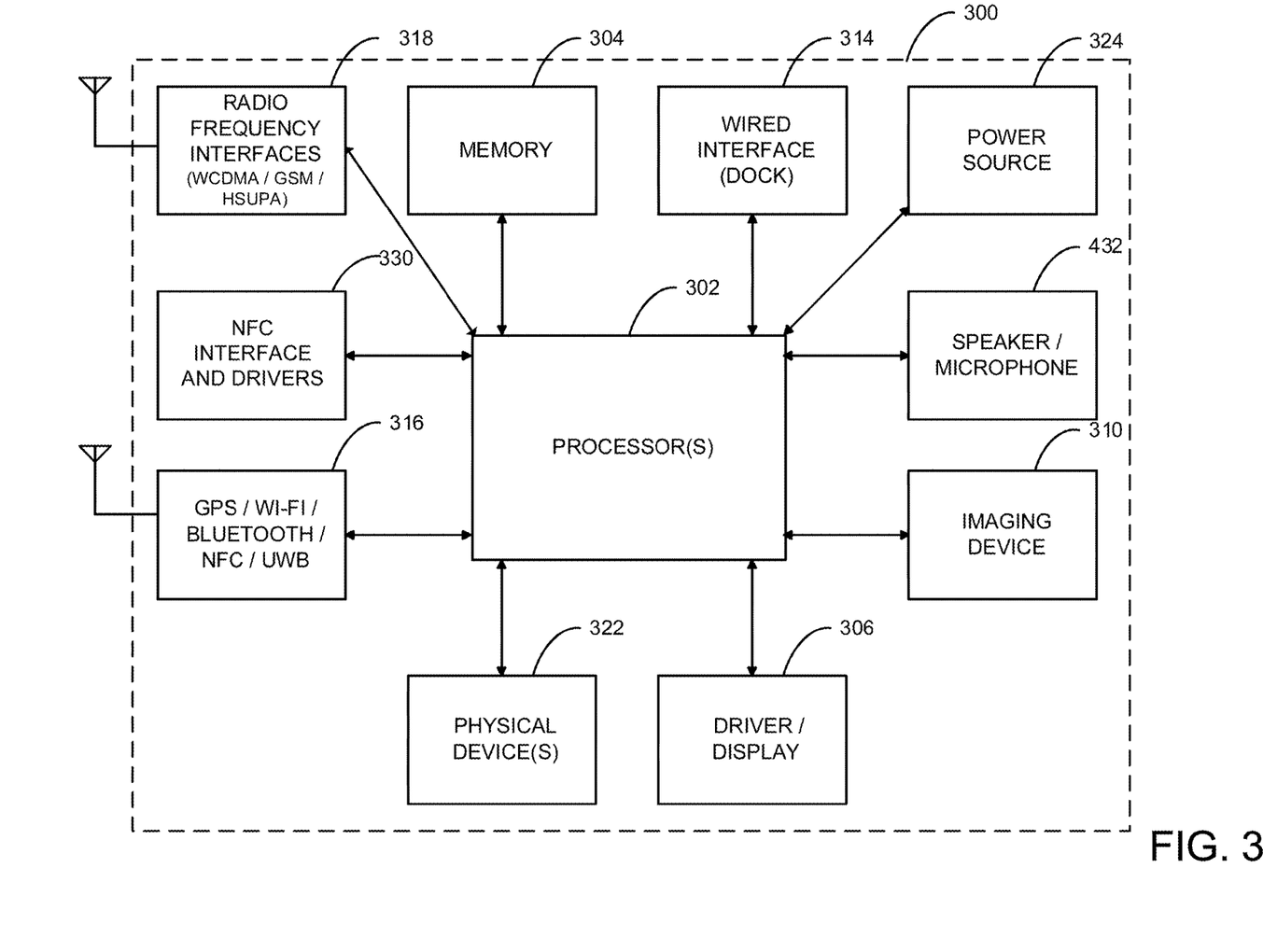
FIG. 3 illustrates a block diagram of various embodiments.

FIG. 3 illustrates a functional block diagram of various embodiments of the present invention. More specifically, it is contemplated that from user smart devices (e.g. smart wearable devices, smart phones, tablets), to laptops, to cloud-based servers, etc. may be implemented with a subset or superset of the below illustrated components.

In FIG. 3, a computing device 300 may include some, but not necessarily all of the following components: an applications processor 302, memory 304, a display 306, an image acquisition device 310, audio input/output devices 312, and the like. Additional communications from and to computing device 300 can be provided by via a wired interface 314 (e.g. dock, plug, controller interface to peripheral devices); a GPS/Wi-Fi/Bluetooth interface/UWB 316; an NFC interface (e.g. antenna or coil) and driver 318; RF interfaces and drivers 320, and the like. Also included in some embodiments are physical sensors 322 (e.g. (MEMS-based) accelerometers, gyros, magnetometers, pressure sensors, temperature sensors, bioimaging sensors etc.).

In various embodiments, computing device 300 may be a computing device (e.g. Apple iPad, Microsoft Surface, Samsung Galaxy Note, an Android Tablet); a smart phone (e.g. Apple iPhone, Google Pixel, Samsung Galaxy S); a portable computer (e.g. netbook, laptop, convertible), a media player (e.g. Apple iPod); a reading device (e.g. Amazon Kindle); a fitness tracker (e.g. Fitbit, Apple Watch, Garmin or the like); a headset or glasses (e.g. Oculus Rift, HTC Vive, Sony PlaystationVR, Magic Leap, Microsoft HoloLens); a wearable device (e.g. Motiv smart ring, smart headphones); an implanted device (e.g. smart medical device), a POS device, a server or the like. Typically, computing device 300 may include one or more processors 302. Such processors 302 may also be termed application processors, and may include a processor core, a video/graphics core, and other cores. Processors 302 may include processor from Apple (A13, A14), NVidia (Tegra), Intel (Core), Qualcomm (Snapdragon), Samsung (Exynos), ARM (Cortex), MIPS technology, a microcontroller, and the like. In some embodiments, processing accelerators may also be included, e.g. an AI accelerator, Google (Tensor processing unit), a GPU, or the like. It is contemplated that other existing and/or later-developed processors/microcontrollers may be used in various embodiments of the present invention.

In various embodiments, memory 304 may include different types of memory (including memory controllers), such as flash memory (e.g. NOR, NAND), SRAM, DDR SDRAM, or the like. Memory 304 may be fixed within computing device 300 and may include removable (e.g. SD, SDHC, MMC, MINI SD, MICRO SD, CF, SIM). The above are examples of computer readable tangible media that may be used to store embodiments of the present invention, such as computer-executable software code (e.g. firmware, application programs), security applications, application data, operating system data, databases or the like. Additionally, in some embodiments, a secure device including secure memory and/or a secure processor are provided. It is contemplated that other existing and/or later-developed memory and memory technology may be used in various embodiments of the present invention.

In various embodiments, display 306 may be based upon a variety of later-developed or current display technology, including LED or OLED status lights; touch screen technology (e.g. resistive displays, capacitive displays, optical sensor displays, electromagnetic resonance, or the like); and the like. Additionally, display 306 may include single touch or multiple-touch sensing capability. Any later-developed or conventional output display technology may be used for embodiments of the output display, such as LED IPS, OLED, Plasma, electronic ink (e.g. electrophoretic, electrowetting, interferometric modulating), or the like. In various embodiments, the resolution of such displays and the resolution of such touch sensors may be set based upon engineering or non-engineering factors (e.g. sales, marketing). In some embodiments, display 306 may integrated into computing device 300 or may be separate. In some embodiments, display 306 may be in virtually any size or resolution, such as a 4K resolution display, a microdisplay, one or more individual status or communication lights, e.g. LEDs, or the like.

In some embodiments of the present invention, acquisition device 310 may include one or more sensors, drivers, lenses and the like. The sensors may be visible light, infrared, and/or UV sensitive sensors, ultrasonic sensors, or the like, that are based upon any later-developed or convention sensor technology, such as CMOS, CCD, or the like. In some embodiments of the present invention, image recognition algorithms, image processing algorithms or other software programs for operation upon processor 302, to process the acquired data. For example, such software may pair with enabled hardware to provide functionality such as: facial recognition (e.g. Face ID, head tracking, camera parameter control, or the like); fingerprint capture/analysis; blood vessel capture/analysis; iris scanning capture/analysis; otoacoustic emission (OAE) profiling and matching; and the like. In additional embodiments of the present invention, acquisition device 310 may provide user input data in the form of a selfie, biometric data, or the like.

In various embodiments, audio input/output 312 may include conventional microphone(s)/speakers. In various embodiments, voice processing and/or recognition software may be provided to applications processor 302 to enable the user to operate computing device 300 by stating voice commands. In various embodiments of the present invention, audio input 312 may provide user input data in the form of a spoken word or phrase, or the like, as described above. In some embodiments, audio input/output 312 may be integrated into computing device 300 or may be separate.

In various embodiments, wired interface 314 may be used to provide data or instruction transfers between computing device 300 and an external source, such as a computer, a remote server, a POS server, a local security server, a storage network, another computing device 300, a client device, a peripheral device to control (e.g. a security door latch, a turnstile latch, a gate, a status light, etc.), or the like. Embodiments may include any later-developed or conventional physical interface/protocol, such as: USB, micro USB, mini USB, USB-C, Firewire, Apple Lightning connector, Ethernet, POTS, custom dock, or the like. In some embodiments, wired interface 314 may also provide electrical power, or the like to power source 324, or the like. In other embodiments interface 314 may utilize close physical contact of device 300 to a dock for transfer of data, magnetic power, heat energy, light energy, laser energy or the like. Additionally, software that enables communications over such networks is typically provided.

In various embodiments, a wireless interface 316 may also be provided to provide wireless data transfers between computing device 300 and external sources, such as computers, storage networks, headphones, microphones, cameras, or the like. As illustrated in FIG. 3, wireless protocols may include Wi-Fi (e.g. IEEE 802.11 a/b/g/n, WiMAX), Bluetooth, Bluetooth Low Energy (BLE) IR, near field communication (NFC), ZigBee, Ultra-Wide Band (UWB), Wi-Fi, mesh communications, and the like.

GPS receiving capability may also be included in various embodiments of the present invention. As illustrated in FIG. 3, GPS functionality is included as part of wireless interface 316 merely for sake of convenience, although in implementation, such functionality may be performed by circuitry that is distinct from the Wi-Fi circuitry, the Bluetooth circuitry, and the like. In various embodiments of the present invention, GPS receiving hardware may provide user input data in the form of current GPS coordinates, or the like, as described above.

Additional wireless communications may be provided via RF interfaces in various embodiments. In various embodiments, RF interfaces 320 may support any future-developed or conventional radio frequency communications protocol, such as CDMA-based protocols (e.g. WCDMA), GSM-based protocols, HSUPA-based protocols, G4, G5, or the like. In some embodiments, various functionality is provided upon a single IC package, for example the Marvel PXA330 processor, and the like. As described above, data transmissions between a smart device and the services may occur via Wi-Fi, a mesh network, 5G, 4G or the like.

In various embodiments, any number of future developed, current operating systems, or custom operating systems may be supported, such as iPhone OS (e.g. iOS), Google Android, Linux, Windows, MacOS, or the like. In various embodiments of the present invention, the operating system may be a multi-threaded multi-tasking operating system. Accordingly, inputs and/or outputs from and to display 306 and inputs/or outputs to physical sensors 322 may be processed in parallel processing threads. In other embodiments, such events or outputs may be processed serially, or the like. Inputs and outputs from other functional blocks may also be processed in parallel or serially, in other embodiments of the present invention, such as acquisition device 310 and physical sensors 322.

In some embodiments of the present invention, physical sensors 322 (e.g. MEMS-based) accelerometers, gyros, magnetometers, pressure sensors, temperature sensors, imaging sensors (e.g. blood oxygen, heartbeat, blood vessel, iris data, etc.), thermometer, otoacoustic emission (OAE) testing hardware, and the like may be provided. Embodiments or such smart devices described herein include smart rings, earbuds, smart glasses, smart watches, and the like, that typically include sensors contact or see the user's skin. The data from such sensors may be used to capture data associated with device 300, and a user of device 300. Such data may include physical motion data, pressure data, orientation data, or the like. Data captured by sensors 322 may be processed by software running upon processor 302 to determine characteristics of the user, e.g. gait, gesture performance data, or the like and used for user authentication purposes. In some embodiments, sensors 322 may also include physical output data, e.g. vibrations, pressures, and the like.

In some embodiments, a power supply 324 may be implemented with a battery (e.g. LiPo), ultracapacitor, or the like, that provides operating electrical power to device 300. In various embodiments, any number of power generation techniques may be utilized to supplement or even replace power supply 324, such as solar power, liquid metal power generation, thermoelectric engines, rf harvesting (e.g. NFC) or the like.

FIG. 3 is representative of components possible for a smart reader, a smart device, an authentication service server, a transaction service server, and the like for embodying different embodiments. It will be readily apparent to one of ordinary skill in the art that many other hardware and software configurations are suitable for use with the present invention. Embodiments of the present invention may include at least some but need not include all of the functional blocks illustrated in FIG. 3. For example, a smart phone (e.g. access control device) configured to perform may of the functions described above includes most if not all of the illustrated functionality. As another example, a wearable device, e.g. a smart ring (electronic devices enclosed in a ring-shaped shell, enclosure, or form factor), may include some of the functional blocks in FIG. 3, but it need not include a high-resolution display 330 or a touch screen, a speaker/microphone 360, wired interfaces 370, or the like. In still other examples, a cloud-based server or a virtual machine (VM) may not include image acquisition device 312, MEMS devices 322, GPS capability 316, and the like, further components described above may be distributed among multiple computers, virtual machines, or the like.

Therefore, it is to be understood that the present disclosure is not to be limited to the specific examples illustrated and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims. Accordingly, parenthetical reference numerals in the appended claims are presented for illustrative purposes only and are not intended to limit the scope of the claimed subject matter to the specific examples provided in the present disclosure.

Further embodiments can be envisioned to one of ordinary skill in the art after reading this disclosure. In other embodiments, combinations or sub-combinations of the above disclosed invention can be advantageously made. The block diagrams of the architecture and flow charts are grouped for ease of understanding. However, it should be understood that combinations of blocks, additions of new blocks, re-arrangement of blocks, and the like are contemplated in alternative embodiments of the present invention.

The specification and drawings are, accordingly, to be regarded in an illustrative rather than a restrictive sense. It will, however, be evident that various modifications and changes may be made thereunto without departing from the broader spirit and scope of the invention as set forth in the claims. More specifically, the claims provide additional disclosure regarding contemplated additional methods of operation, methods for fabrication, additional components and functionalities, and apparatus according to various embodiments of the present invention.

We claim:

1. A method for fabricating a smart ring comprising:
receiving a printed circuit board having a plurality of components including a processor, a memory, a temperature sensor, a wireless transceiver, and a perturbation sensor;
receiving a power source characterized by a first radius of curvature within a range of 9 mm to 13 mm;
coupling the printed circuit board and the power source together to form a first assembly characterized by the first radius of curvature;
encapsulating at least a first portion of the first assembly to form a flexible second assembly, wherein a flexibility of the flexible second assembly enables the flexible second assembly to be compatible with a plurality of fixed band sizes, each fixed band size corresponding to a respective ring size within a first range of ring sizes spanning a plurality of ring sizes, wherein the flexible second assembly includes a plurality of physical anchors; and
coupling a rigid band associated with a first fixed band size of the plurality of fixed band sizes to the flexible second assembly via the plurality of physical anchors to form an enclosed circle-like shape that permanently fixes the smart ring to a rigid, non-adjustable ring size included within the plurality of ring sizes, the non-adjustable ring size corresponding to the first fixed band size.

2. The method of claim 1 wherein encapsulating the first portion of the first assembly comprises:
receiving an upper enclosure and a lower enclosure;
disposing the first assembly between the upper enclosure and the lower enclosure;
coupling the upper enclosure to the lower enclosure; and
wherein the upper enclosure and the lower enclosure together form an interior region for the first assembly;
wherein the upper enclosure comprises a material that inhibits bending of the first assembly.

3. The method of claim 2 wherein receiving the upper enclosure and the lower enclosure comprises:
receiving the upper enclosure, wherein the upper enclosure is characterized by an outer radius of curvature that is compatible with a plurality of ranges of ring sizes, including at least the first range of ring sizes spanning the plurality of ring sizes and a second range of ring sizes spanning a different plurality of ring sizes; and
selecting a first lower enclosure from a set of lower enclosures based at least in part on the non-adjustable ring size being included within the plurality of ring sizes, the set of lower enclosures including at least the first lower enclosure associated with the first range of ring sizes and a second lower associated with the second range of ring sizes.

4. The method of claim 1 wherein encapsulating the first portion of the first assembly comprises:
disposing the first assembly within a mold; and
injecting a material within the mold.

5. The method of claim 1 wherein coupling the rigid band to the flexible second assembly comprises:
disposing the flexible second assembly within a mold; and
injecting a material within the mold to thereby overmold the material over the plurality of physical anchors and to form the rigid band, wherein the material is selected from a group consisting of: silicone material, rubber, plastic, and epoxy.

6. The method of claim 1 wherein coupling the rigid band to the flexible second assembly comprises:
receiving a pre-formed band associated with the non-adjustable ring size; and
coupling the band to the flexible second assembly via the plurality of physical anchors.

7. The method of claim 1 further comprising:
receiving a bare printed circuit board;
disposing the plurality of components upon the bare printed circuit board; and
disposing an encapsulant above the plurality of components.

8. The method of claim 1 wherein the wireless transceiver is selected from a group consisting of: Bluetooth, Bluetooth Low Energy (BLE), ZigBee, ultrawide band (UWB), radio frequency (RF), laser, optical, and near field communication (NFC).

9. The method of claim 1:
wherein encapsulating the first portion of the first assembly further comprises inhibiting encapsulating a second portion of the first assembly;
wherein the second portion is selected from a group consisting of: metal electrodes, light input/output guides or pipes, metallic sensors, ceramic sensors, capacitive sensors, and infrared sensors and imaging sensors.

10. The method of claim 1 wherein the rigid band comprises a plurality of anchor points configured to be coupled to the plurality of physical anchors.

11. A smart ring comprising:
a first assembly characterized by a rigid, non-adjustable ring size included within a plurality of ring sizes, the non-adjustable ring size corresponding to a first fixed band size of a plurality of fixed band sizes, wherein each fixed band size corresponds to a respective ring size within the plurality of ring sizes, wherein the non-adjustable ring size is permanently fixed to the non-adjustable ring size in response to coupling a rigid band associated with the first fixed band size to a flexible second assembly via a plurality of physical anchors to form an enclosed circle-like shape, the first assembly comprising:
the flexible second assembly characterized by an inner radius of curvature within a range of 9 mm to 13 mm, wherein a flexibility of the flexible second assembly enables the flexible second assembly to be compatible with each fixed band size of the plurality of fixed band sizes, the flexible second assembly comprising:
a printed circuit board having a plurality of components including a processor, a memory, a temperature sensor, a wireless transceiver and a perturbation sensor;
a power source;
a plurality of interconnects coupled between the printed circuit board and the power source;
an encapsulating material disposed about at least a first portion of the flexible second assembly;
the plurality of physical anchors; and
the rigid band coupled to the first assembly via the plurality of physical anchors forming the enclosed circle-like shape that permanently fixes the smart ring to the rigid, non-adjustable ring size included within the plurality of ring sizes.

12. The smart ring of claim 11:
wherein the encapsulating material comprises an upper enclosure and a lower enclosure that are coupled to form an interior region where the first portion of the flexible second assembly is disposed;
wherein the upper enclosure comprises a material that inhibits bending of the first assembly.

13. The smart ring of claim 12:
wherein the upper enclosure is characterized by an outer radius of curvature that is compatible with a plurality of ranges of ring sizes, including at least a first range of ring sizes spanning the plurality of ring sizes and a second range of ring sizes spanning a different plurality of ring sizes;
wherein the lower enclosure comprises a first lower enclosure selected from a set of lower enclosures, the set of lower enclosures including at least the first lower enclosure associated with the first range of ring sizes and a second lower associated with the second range of ring sizes.

14. The smart ring of claim 12:
wherein the rigid band comprises a material over molded upon the plurality of physical anchors;
wherein the material is selected from a group consisting of: silicone material, rubber, plastic, and epoxy.

15. The smart ring of claim 11:
wherein the rigid band is pre-formed and comprises a plurality of anchoring regions;
wherein the plurality of physical anchors are configured to be physically coupled to and decoupled from the plurality of anchoring regions.

16. The smart ring of claim 11 wherein the wireless transceiver is selected from a group consisting of: Bluetooth, Bluetooth Low Energy (BLE), ZigBee, ultrawide band (UWB), radio frequency (RF), laser, optical and near field communication (NFC).

17. The smart ring of claim 11 wherein the encapsulating material is not disposed upon a second portion of the flexible second assembly.

18. The smart ring of claim 17 further comprising:
one or more light-emitting diodes (LEDs);
wherein the second portion is coupled to components selected from a group consisting of: the temperature sensor, the power source and the one or more LEDs.

19. The smart ring of claim 17 wherein the second portion is selected from a group consisting of: metal electrodes, light input/output guides or pipes, metallic sensors, ceramic sensors, capacitive sensors, infrared sensors, fingerprint sensors, ultrasonic sensors, and imaging sensors.

20. The smart ring of claim 11 wherein the encapsulating material is transparent.

\* \* \* \* \*